United States Patent [19]
Paniccia

[11] Patent Number: 5,930,588
[45] Date of Patent: Jul. 27, 1999

[54] METHOD FOR TESTING AN INTEGRATED CIRCUIT DEVICE

[75] Inventor: Mario J. Paniccia, Santa Clara, Calif.

[73] Assignee: Intel Corporation, Santa Clara, Calif.

[21] Appl. No.: 09/041,372

[22] Filed: Mar. 11, 1998

Related U.S. Application Data

[62] Division of application No. 08/778,019, Dec. 31, 1996.

[51] Int. Cl.$^6$ ............................ G01R 31/26; H01L 21/66
[52] U.S. Cl. .................................. 438/16; 438/14; 438/15
[58] Field of Search ................................. 438/16, 14, 15

[56] References Cited

U.S. PATENT DOCUMENTS

| | | | |
|---|---|---|---|
| 4,758,092 | 7/1988 | Heinrich et al. | 356/364 |
| 5,262,355 | 11/1993 | Nzsuzguchz et al. | 438/106 |
| 5,277,769 | 1/1994 | Medernach | 438/14 |
| 5,564,830 | 10/1996 | Böbel et al. | 438/16 |

OTHER PUBLICATIONS

Jacques I. Pankove, Optical Processes In Semiconductors, Dover Publications, Inc., New York, 1971, Properties Of Semiconductors Tables.

H.K. Heinrich, et al., "Optical Detection of Multibit Logic Signals at Internal Nodes in a Flip–Chip mounted Silicon Static Random–Access Memory Integrated Circuit", *Journal Vacuum, Science and Technology*, vol. 10, No. 6, pp. 3109–3111, Nov.–Dec.1992.

Melle Griot Catalogue Introductory Chapter, "Optical Coatings", Chapter 5, pp. 5:1–5:40, 1995.

H.K. Heinrich, et al., "Noninvasive Sheet Charge Density Probe for Integrated Silicon Devices", *Appl. Phys. Lett. 48 (16), American Institute of Physics*, pp. 1066–1068, Apr. 21, 1986.

Marvin Chester, et al., "Electroabsorption Spectrum in Silicon", *University of California, LA, Physical Review Letters*, vol. 13, No. 6, pp. 193–195, Aug. 10, 1964.

*Primary Examiner*—Kevin M. Picardat
*Assistant Examiner*—Deven Collins
*Attorney, Agent, or Firm*—Blakely, Sokoloff, Taylor & Zafman

[57] ABSTRACT

A method for testing an integrated circuit situated on the top of a semiconductor substrate. The method includes the steps of focusing a photon onto a portion of the integrated circuit through an anti-reflective coating disposed on the back side of the semiconductor substrate and detecting the photon after the photon is reflected from the integrated circuit.

23 Claims, 8 Drawing Sheets

METHOD FOR TESTING AN INTEGRATED CIRCUIT DEVICE

This is a divisional of application Ser. No. 08/778,019, filed Dec. 31, 1996.

FIELD OF THE INVENTION

The present invention relates generally to integrated circuit testing and, more specifically, to the enhancement of optical-based testing of integrated circuits.

BACKGROUND OF THE INVENTION

Within the integrated circuit industry there is a continuing effort to increase integrated circuit speed as well as device density. As a result of these efforts, there is a trend towards using flip chip technology when packaging complex high speed integrated circuits. Flip chip technology is also known as control collapse chip connection (C4) packaging. In C4 packaging technology, the integrated circuit die is flipped upside down. This is opposite to how integrated circuits are packaged today using wire bond technology. By flipping the die upside down, ball bonds may be used to provide direct electrical connections from the bond pads directly to the pins of the package.

In the following discussion reference will be made to a number of drawings. The drawings are provided for descriptive purposes only and are not drawn to scale.

FIG. 1A illustrates integrated circuit packaging 101 which utilizes wire bonds 103 to electrically connect integrated circuit connections in integrated circuit die 105 through metal interconnects 109 to the pins 107 of package substrate 111. With the trend towards high speed integrated circuits, the inductance generated in the wire bonds 103 of the typical integrated circuit packaging 101 becomes an increasingly significant problem.

FIG. 1B illustrates C4 packaging 151 with the integrated circuit die 155 flipped upside down. In comparison with the wire bonds 103 of FIG. 1A, the ball bonds 153 of C4 packaging 151 provide more direct connections between the integrated circuit die 155 and the pins 157 of package substrate 161 through metal interconnects 159. As a result, the inductance problems associated with typical integrated circuit packaging technologies that use wire bonds are minimized. Unlike wire bond technology, which only allows bonding along the periphery of the integrated circuit die, C4 technology allows connections to be placed anywhere on the integrated circuit die surface. This leads to very low inductance and better power distribution to the integrated circuit which is another major advantage of C4.

A consequence of the integrated circuit die 155 being flipped upside down in C4 packaging 151 is that access to internal nodes of the integrated circuit die 155 for testing purposes has become a considerable challenge. In particular, during the silicon debug phase of a new product that is designed to be packaged into C4, it is often necessary to probe electrical signals from internal nodes of the chip, insitu, while the chip is packaged in its native C4 packaging environment. During the debug process it is often necessary to probe certain internal nodes in order to obtain important electrical data from the integrated circuit. Important data include measuring device parameters such as, but not limited to, voltage levels, timing information, current levels and thermal information.

Present day debug process for wire bond technology is based on directly probing the metal interconnects on the chip front side with an electron beam (E-beam) or mechanical prober. Typical integrated circuit devices have multiple layers of metal interconnects and it is often difficult to access nodes that are buried deep in the chip. Usually other tools such as plasma etchers and focused ion beam systems must be used to mill away the dielectric and or metal above the node to expose nodes for probing.

With C4 packaging technology, however, this front side methodology is not feasible since the integrated circuit die is flipped upside down. As illustrated in FIG. 1B, access to the metal interconnects 159 for the purpose of conventional probing is obstructed by the package substrate 161. Instead, the P-N junctions forming the diffusion regions 163 of the integrated circuit are accessible through the back side of the silicon substrate of integrated circuit die 155. There are a number of potential optical-based applications that can be used to debug C4 mounted semiconductor devices. FIG. 2 illustrates a prior art method used to probe active diffusion regions in integrated circuits. In the setup shown in FIG. 2, an integrated circuit device 231 includes an active region 239 and non active region (metal) 241. An infrared laser 221 is positioned to focus a laser beam 223 through a beam splitter 225, a birefringent beam splitter 227 and an objective lens 229 through the back side of the integrated circuit device 231 on the diffusion region 239 and metal 241. As shown in FIG. 2, birefringent beam splitter 227 separates the laser beam 223 into two separate laser beams, a probe laser beam 235 and reference laser beam 237. Both probe laser beam 235 and reference laser beam 237 are reflected from active region 239 and metal 241, respectively, back through objective lens 229 into birefringent beam splitter 227. Probe laser beam 235 and reference laser beam 237 are then recombined in birefringent beam splitter 227 and are guided into detector 233 through beam splitter 225.

By operating the integrated circuit device 231 while focusing probe laser beam 235 on active region 239 and reference laser beam 237 on metal 241, timing waveforms may be detected with detector 233 through the silicon substrate of device 231. Detection is possible due to the plasma-optical effect in which the refractive index of a region of charge is different to a region with no charge. The application of a bias causes the charge, and hence the refractive index, in the probed region to be modulated whereas the refractive index of the region under the reference beam is unaltered. This results in phase shift between probe beam 235 and reference beam 237. Accordingly, by measuring the phase difference between the reflected reference beam 237 and probe laser beam 235, detector 233 is able to generate an output signal 241 that is proportional to the charge modulation caused by operation of the P-N junction region under the probe. This optical measurement can then be combined with conventional stroboscopic techniques to measure high frequency charge and hence voltage waveforms from the P-N junction region 239.

Other optical-based applications, such as optical-based imaging through silicon using an infrared laser scan microscope, thermal mapping, temperature probing, etc., can be used in the testing of integrated circuits) by focusing a light source onto a portion of the circuit (e.g., a diffusion area, P-N junction, metal contact, metal interconnect, etc.) and monitoring the reflected light. For instance, thermal mapping or temperature probing may be accomplished by directing a laser beam onto a metal interconnect, or other portion of the integrated circuit, and detecting the index of refraction change due to temperature fluctuations in the integrated circuit.

Another type of optical-based testing method involves the use of an infra-red camera 350 that is positioned to detect photon emissions 302 from the back side surface 304 of a semiconductor substrate 305 containing an integrated circuit device 306, as illustrated in FIG. 3. The detection of back side photon emissions is useful in determining a variety of circuit related defects, such as, but not limited to, impact ionization, shorts, hot carrier effects, forward and reverse bias junctions, transistors in saturation, and gate oxide breakdown.

Due to high doping concentrations found in present day semiconductor devices, however, there is a significant reduction in the transmission of energy traveling through the highly doped semiconductor substrate. Reflections at the semiconductor-air interface also cause a significant reduction in the transmission of light through the back side of the semiconductor substrate. As shown in FIG. 4, the intensity of an incident infrared beam 402 directed into a semiconductor substrate 410 by a laser 400 is reduced as the beam passes through the semiconductor back side surface 412. As shown in FIG. 4, a portion of the beam's energy is directed into the substrate while another portion of the beam is reflected off the substrate's back side surface 412. In silicon, a laser beam having a wavelength of 1064 nanometers loses about a third of it's energy at the semiconductor-air interface due to reflection at the surface. This is due to the index of refraction difference between air and silicon. The transmitted beam 404 passes through silicon substrate 410 and is reflected off a metal contact or metal interconnect line 414 and back out the back side surface of the semiconductor substrate. About one third of the reflected energy 404 is again lost as the beam passes through the back side surface 412 of the semiconductor substrate. Ignoring energy losses due to absorption and scattering effects, the total energy of the transmitted beam 406 is less than half the intensity of the incident beam 402.

Reflection at the semiconductor back side surface also affects the number of photon emissions which make it across the silicon/air surface interface. Turning again to FIG. 3, in a semiconductor substrate 305 comprising silicon, about one third of the photon emissions 303 are lost due to reflection at the silicon-air interface at surface 304.

The use of optical-based debugging and testing techniques may require a thinning of the backside of the integrated circuit semiconductor in order to offset the effects of absorption in the semiconductor substrate. Thinning of the semiconductor substrate increases the intensity of photon emissions from the integrated circuit by reducing the loss of energy due to absorption in the semiconductor substrate. Significant thinning of the semiconductor substrate, however, could prohibit testing of the integrated circuit at full speed due to device performance degradation and reduced power dissipation through the remaining thinned silicon substrate.

Therefore, what is needed is a method and an apparatus that enhances the use of optical-based techniques used in the debugging and testing of integrated circuits devices through the backside of a semiconductor.

SUMMARY OF THE INVENTION

A method for testing an integrated circuit situated on the top of a semiconductor substrate is disclosed. The method includes the steps of focusing a photon onto a portion of the integrated circuit through an anti-reflective coating disposed on the back side of the semiconductor substrate and detecting the photon after the photon is reflected from the integrated circuit surface.

BRIEF DESCRIPTION OF THE DRAWINGS

The present invention is illustrated by way of example and is not limited by the figures of the accompanying drawings, in which like references indicate similar elements, and in which.

DETAILED DESCRIPTION

An apparatus and method for reducing the reflection of light off the surface of a semiconductor device under test is described. In the following description, numerous specific details are set forth such as material types, dimensions, processing steps, etc., in order to provide a thorough understanding of the present invention. However, it will be obvious to one of skill in the art that the invention may be practiced without these specific details. In other instances, well known elements and processing techniques have not been shown in particular detail in order to avoid unnecessarily obscuring the present invention.

Whenever light is incident on the boundary between two media, for example air and silicon, some of the light is reflected at the surface of the silicon and some of the light is transmitted into the silicon. Reflection at the boundary occurs due to a mismatch of the indices of refraction between the silicon and air. When a beam of light is incident normal to a plane surface, the ratio of the percent light reflected and percent light transmitted is determined by the refractive index of the two different media. The intensity of the reflected light beam is given by the following relationship:

$$R = [(N_2-N_1)/(N_2+N_1)]^2 \quad \text{(Equation 1)}$$

where R represents the intensity of the reflected light beam in relation to the incident light beam, $N_1$ is the index of refraction of a first media and $N_2$ is the index of refraction of a second media. At the boundary of a air-silicon interface, $N_1$ is the refraction index of air and $N_2$ is the refraction index of silicon. From Equation 1, it can be seen that the amount of light that is reflected at the boundary is therefore larger when the disparity between the two indices of refraction is greater. Conversely, the amount of light reflected at the boundary is lower when the disparity between the indices of refraction is lower. At an air-silicon interface where $N_{air}=1$ and $N_{silicon}>3.5$, the intensity of the reflected beam is reduced by more than 30 percent (R>0.3).

Figure 1A:
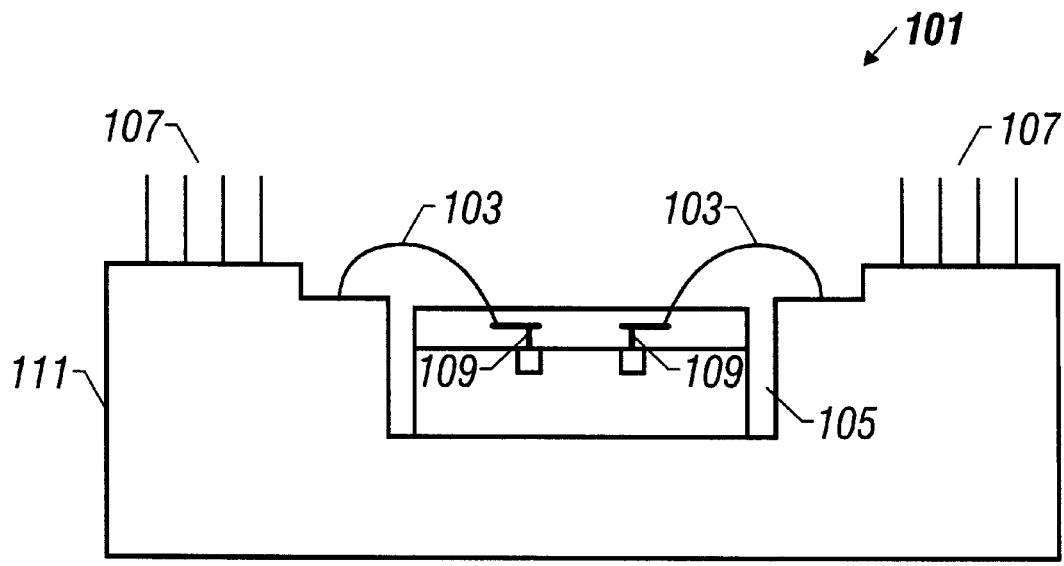
FIG. 1A illustrates a semiconductor device that is wire bonded to a package.
Figure 1B:
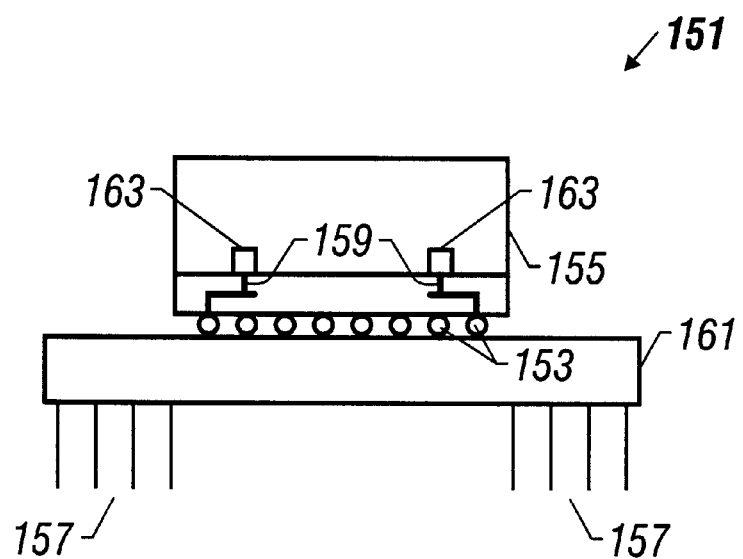
FIG. 1B illustrates a semiconductor device that is mounted to a package using flip chip or C4 technology.
Figure 2:
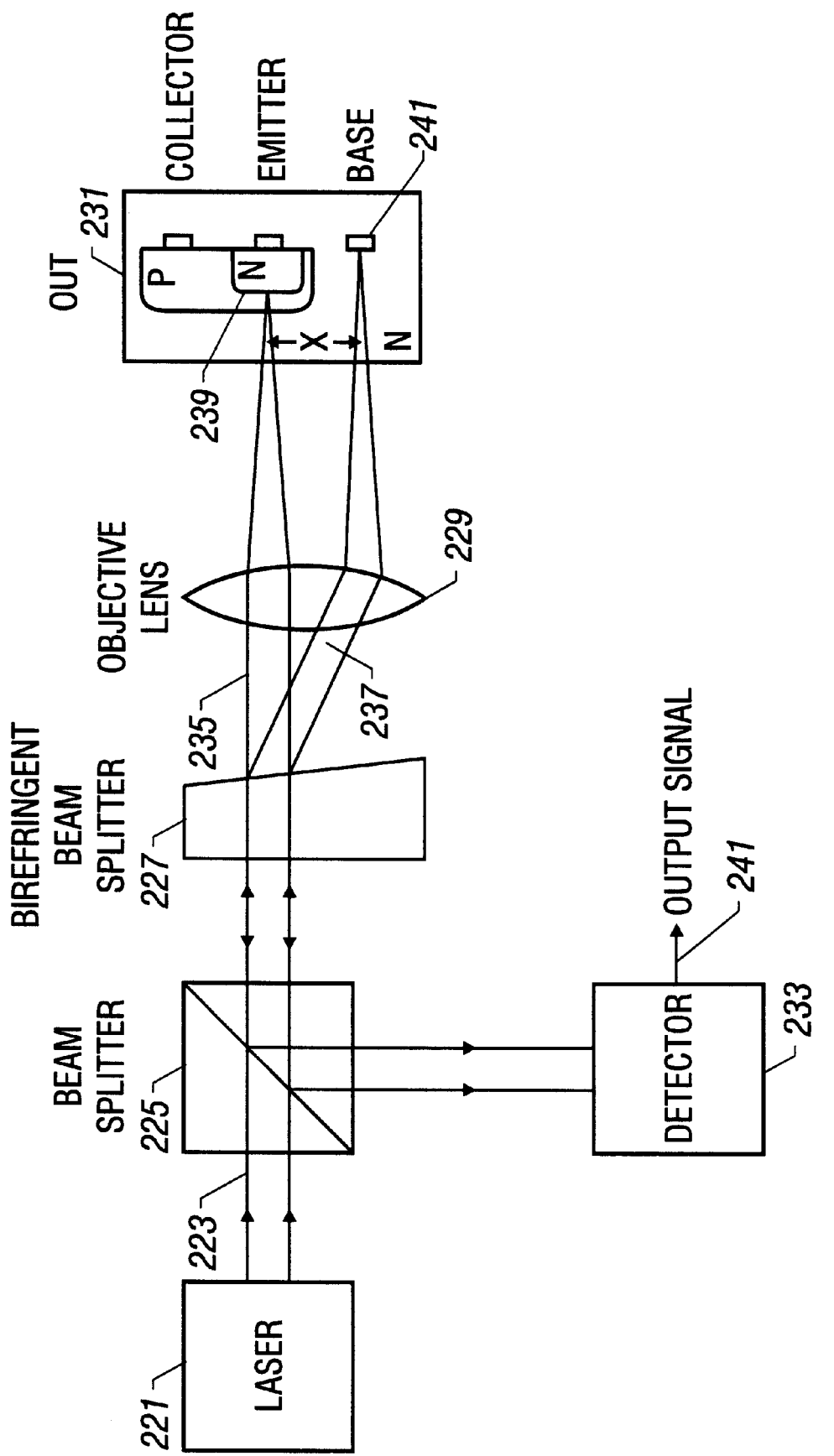
FIG. 2 illustrates a prior art optical-based probing technique used in debugging and testing integrated circuits.
Figure 3:
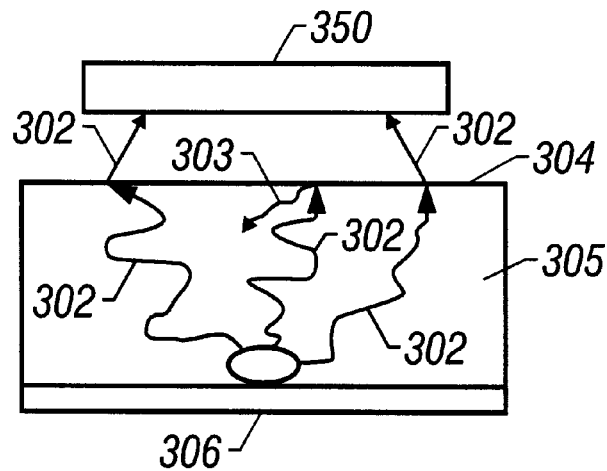
FIG. 3 illustrates a prior art method of detecting emissions from the back side of a semiconductor device.
Figure 4:
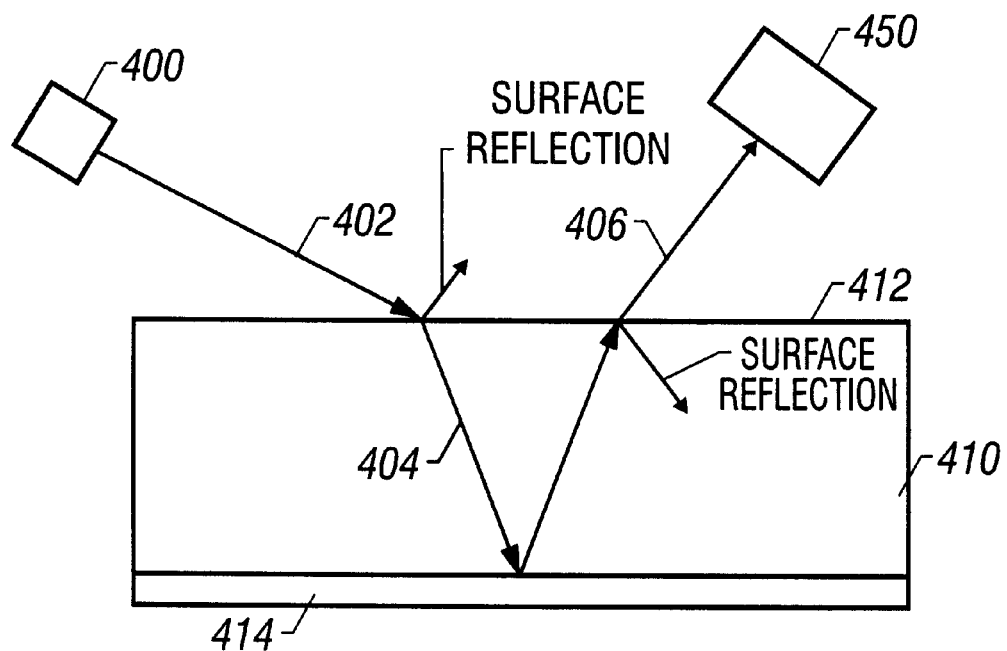
FIG. 4 shows the surface reflection of a light beam as it passes through the surface of a semiconductor.

As previously discussed, a problem associated with the use of optical-based techniques in the field of semiconductor testing arises due to the reflection of light at the surface of the semiconductor substrate. Reflection at the semiconductor surface weakens the intensity of the energy being emitted from the surface making it more difficult to detect the emitted photons. Reflection also limits the amount of returning laser power that is injected into the silicon substrate. (See FIG. 4.)

Figure 5A:
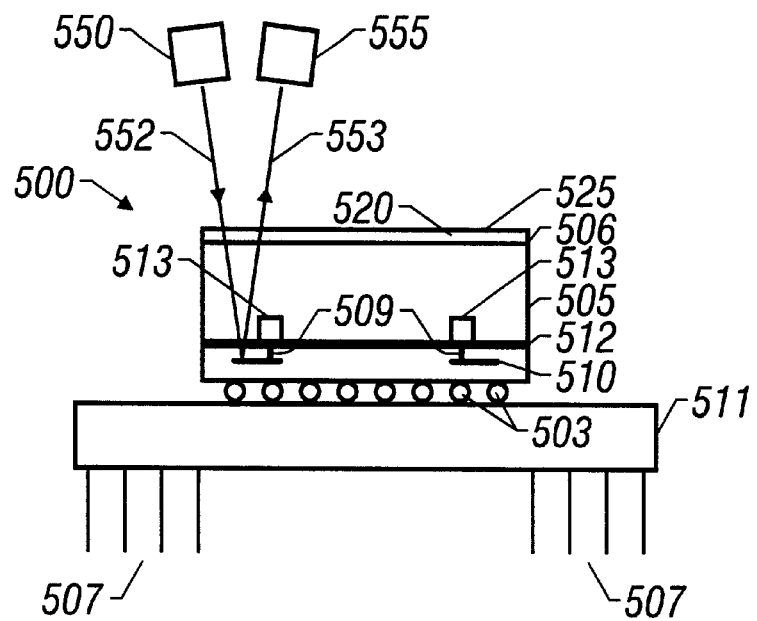
FIG. 5A illustrates a C4 mounted semiconductor device being probed by a laser in accordance with one embodiment of the present invention.

FIG. 5A illustrates a semiconductor device in one embodiment of the present invention, and a method of testing the same. As illustrated, a semiconductor device 500 is C4 mounted to a package 511 via a plurality of ball solder interconnects 503. Pins 507 are used to connect the package to a host device, such as a motherboard. Semiconductor device 500 comprises a semiconductor substrate 505 having an integrated circuit formed on the top of the substrate. The integrated circuit comprises diffusion regions 513 and contacts 509 that connect the diffusion regions to metal layer interconnects 510. Diffusion regions 513 are separated from the metal regions behind them with an oxide film 512. In accordance with the present invention, the back side surface 506 of the semiconductor substrate 505 is covered with an anti-reflective coating 520. The anti-reflective coating 520 may be deposited onto the back side surface 506 using a variety of known processes, such as evaporation, electron-beam deposition and/or sputtering. The method that is used to deposit the anti-reflective coating should be chosen such that the process does not affect the performance of the fully packaged component. The refractive index and thickness of coating 520 is selected such that reflections from the outer surface 525 of coating 520 and the outer surface 506 of substrate 505 cancel each other out by a phenomenon known as "destructive interference." For a single layer anti-reflective coating the two reflected beams to be equal in intensity, it is necessary that the refractive index ratio, be the same at both the interfaces. That is, $$\frac{N_{air}}{N_{film}} = \frac{N_{film}}{N_{substrate}} \quad \text{(Equation 2)}$$

where N represents the refractive index of the respective media. Since the refractive index of air is 1.0, the single layer anti-reflective coating ideally should have a refraction index that is equal to the square-root of the refractive index of the semiconductor substrate material. When the refractive indices of the media are perfectly matched in accordance with Equation 2 and the thickness of the single layer coating is made to provide a phase shift of 180 degrees (i.e., destructive interference), the amount of energy reflected at the air-substrate interface should be zero. In order to achieve destructive interference, the thickness, t, of a single layer, anti-reflective coating 520 is determined by the equation:

$$t = \lambda/4N_{film} \quad \text{(Equation 3)}$$

wherein $\lambda$ is the wavelength of photon or laser beam passing through the back side surface of substrate 505, and $N_{film}$ is the refractive index of the anti-reflective coating material. An anti-reflective coating having a thickness, t, ensures that the two reflected waves are 180 degrees out of phase, a requirement that is needed to insure destructive interference.

Figure 6A:
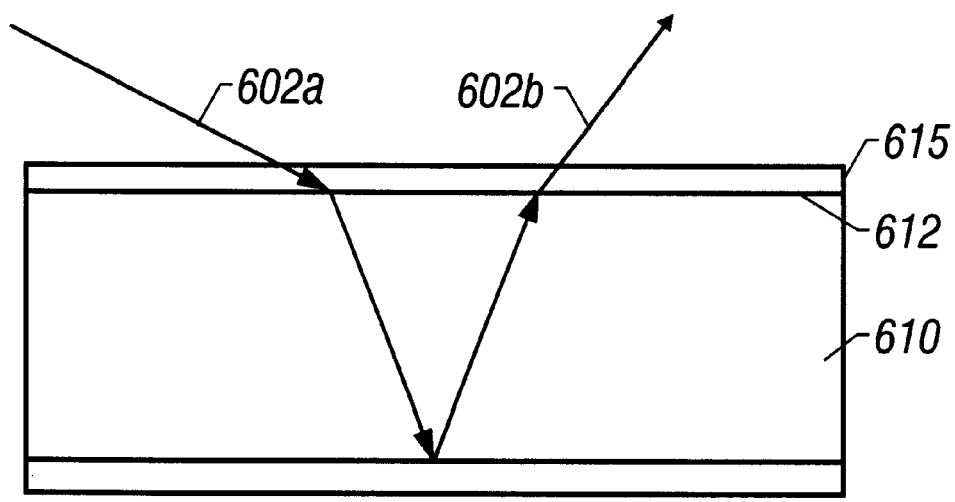
FIG. 6A illustrates an infrared beam that is directed into the back side surface of a semiconductor substrate having an anti-reflective coating deposited onto the back side of the substrate.

As shown in FIG. 6A, when laser beam 602a is directed into a substrate 610 having an anti-reflective film 615 deposited on the back side surface 612, the energy of the laser beam 602b exiting the substrate should be equal to the energy of the photon 602a directed into the substrate (ignoring losses due to absorption and any scattering effects).

Figure 6B:
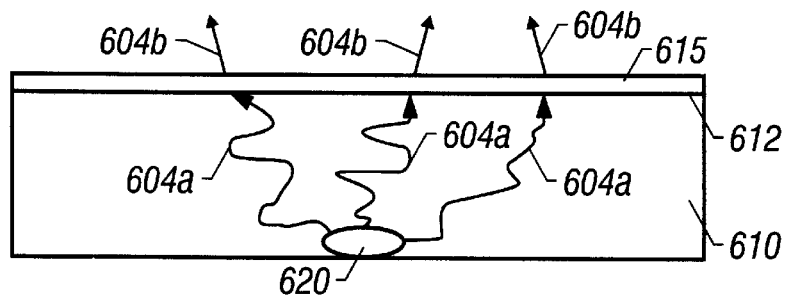
FIG. 6B illustrates a defect that is emitting photons through a semiconductor substrate and through the back side surface of the substrate that is coated with an anti-reflective material.

As illustrated in FIG. 6B, the number of photon emissions 604b exiting substrate 610 at surface 612 is also equal to the number of photons being emitted 604a from a photon source 620 when a proper anti-reflective coating is deposited.

Figure 7:
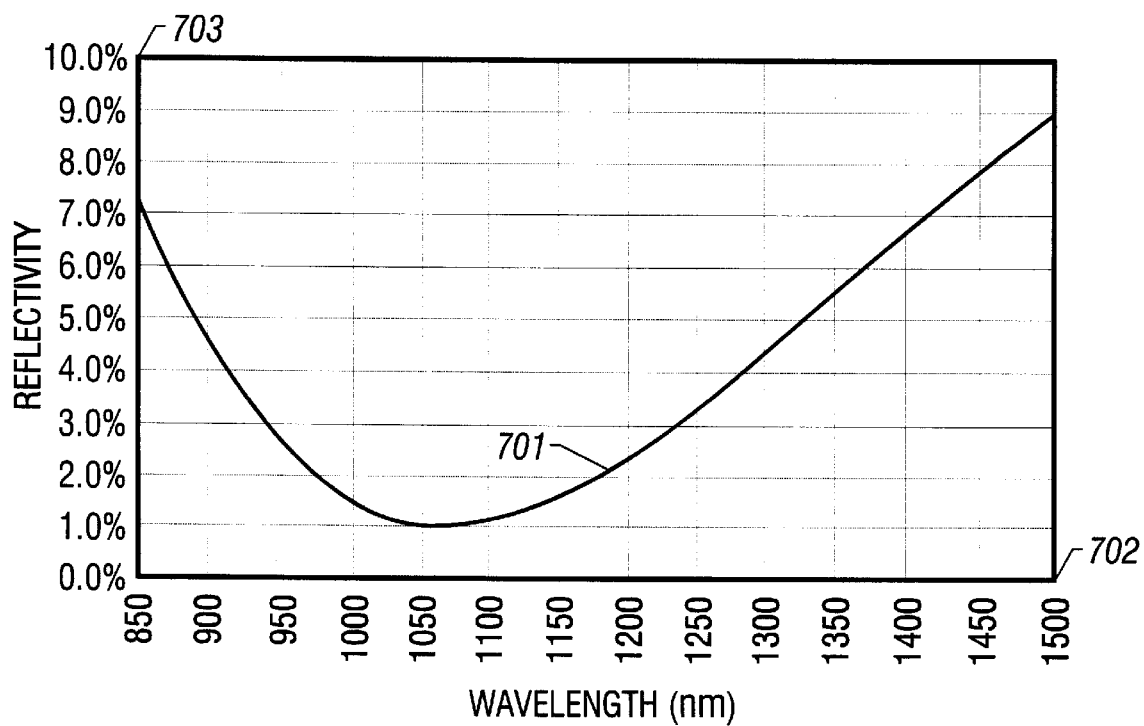
FIG. 7 illustrates a reflectivity curve for an anti-reflective coating in one embodiment of the present invention.

FIG. 7 is a graph of a reflectivity curve 701 for an anti-reflective coating deposited onto a silicon substrate. Axis 702 represents the wavelength of a photon incident on the boundary of the anti-reflective coating. Axis 703 represents the percent of energy reflected at the boundary. In the example of FIG. 7, the anti-reflective coating reduces the reflectivity of a photon having a wavelength of 1064 nanometers to 1% of the total energy incident the substrate and anti-reflective coating boundary. A maximum of less than 7% reflectivity is achieved between the wavelengths of 850 to 1400 nanometers. As previously discussed, the reflectivity of a photon directed through the plane surface of a silicon substrate will be approximately one third (33%) of its incident energy due to reflection at the silicon-air interface. Many optical-based testing methodologies require a light to transcend the silicon surface twice, which results in a total loss of approximately 54% of the light's energy due to reflection at the silicon-air interface. The total loss of energy due to reflection at the silicon surface is reduced to 2% of the photon's energy when the silicon substrate is coated with an anti-reflective film having the reflectivity characteristics of curve 701.

Hence, in accordance with the present invention, the semiconductor device 500 of FIG. 5A may be tested by focusing a beam 552 from a laser 550 onto a portion of the integrated circuit through anti-reflective coating 520 and detecting the intensity of the beam with a detector 555 after it is reflected from the portion of the integrated circuit under test. In FIG. 5A, a metal interconnect 510 is shown being probed by laser 550. Other portions of device 500 may be optically probed in accordance with the methodology of the present invention, such as, for example, diffusion regions 513 and other metal layer interconnects.

Figure 5B:
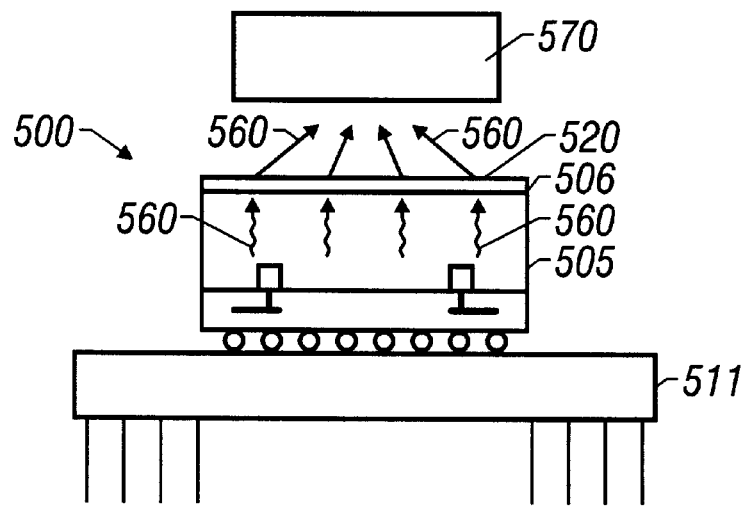
FIG. 5B illustrates another embodiment of the present invention wherein the emissions from a semiconductor device are measured.

It is understood that the present invention is not limited to any particular optical-based testing method, nor is it limited to the testing of any particular portion of an integrated circuit device. As illustrated in FIG. 5B, an infra-red camera 570 may be positioned above semiconductor device 500 to detect photon emissions 560 emanating from the coated back side surface 506 of the device.

Figure 5C:
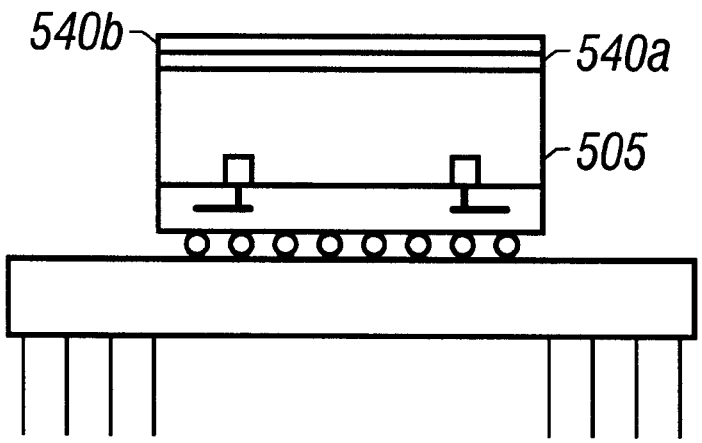
FIG. 5C illustrates the C4 mounted semiconductor device of FIG. 5A having a multi-layered anti-reflective coating deposited onto the back side surface of the semiconductor substrate.

Although the present discussion has thus far been limited to single layer anti-reflective coating applications, it is appreciated that the present invention is not limited to such applications. Multilayer anti-reflective coatings can also provide a reduction in reflectivity while allowing one to change the shape of the reflectivity curve. In addition, a basic problem of a single layer anti-reflective coating is that the refractive index of the coating material is usually high, resulting in too strong a reflection from the top surface of the coating which cannot be completely canceled by interference of the weaker reflection from the back side surface of the semiconductor substrate. Moreover, the availability of materials having a high refractive index is limited. Although the physics and deposition processes surrounding the use of multilayer anti-reflective coatings are more complex than those associated with single layer anti-reflective coating applications, the benefits of using multilayer coatings can, in some instances, outweigh these drawbacks. FIG. 5C illustrates the semiconductor device 500 of FIG. 5A having an anti-reflective coating consisting of two anti-reflective layers 540a and 540b.

The anti-reflective coating may be deposited onto the back side of the semiconductor substrate by any of a variety of processes known in the art. In one embodiment, the anti-reflective coating is evaporated onto the substrate surface. Other processes, such as electron beam depositing, spin-on resist and sputtering may also be used to deposit the anti-reflective coating.

Figure 5D:
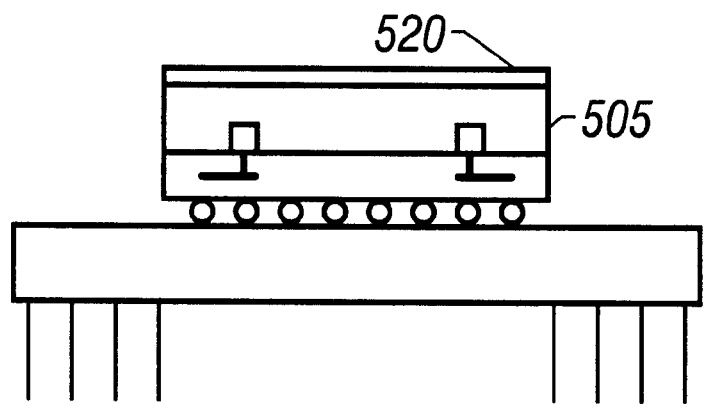
FIG. 5D illustrates the C4 mounted semiconductor device of FIG. 5A with the back side of the semiconductor substrate being globally thinned.

To further enhance the energy level of a photon being emitted from the surface of semiconductor device 500, semiconductor substrate 505 may be globally thinned prior to the application of anti-reflective coating 520, as shown in FIG. 5D. Since absorption losses through semiconductor substrate 505 are exponentially a function of the substrate thickness, these absorption losses may be effectively reduced by the thinning of the semiconductor substrate. In one embodiment, substrate 505 is thinned and then polished to a smooth surface 506. In such an embodiment, substrate 505 may be thinned by first chemically etching and then polishing surface 506 to a shiny finish. Other processes known in the art, such as milling and mechanical grinding may also be used to globally thin substrate 505.

Figure 5E:
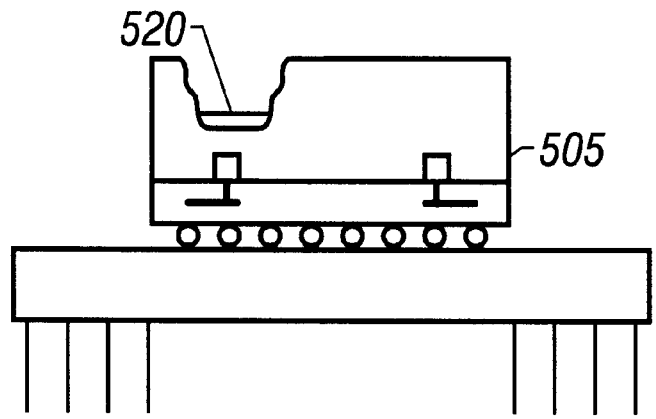
FIG. 5E illustrates the C4 mounted semiconductor device of FIG. 5A with the back side of the semiconductor substrate being locally thinned.

In some instances it is not necessary to test all portions of an integrated circuit. In such instances, a localized thinning of semiconductor substrate 505, rather than a global thinning, may be preferred. Accordingly, as depicted in FIG. 5E, substrate 505 may be thinned only at points residing above the portion(s) of the integrated circuit to be tested. Once the substrate is thinned, an anti-reflective coating 520 may be deposited into the localized thinned area. Localized thinning of the substrate may be accomplished by any of a variety of processes known in the art, such as etching, polishing, milling, etc.

Figure 8A:
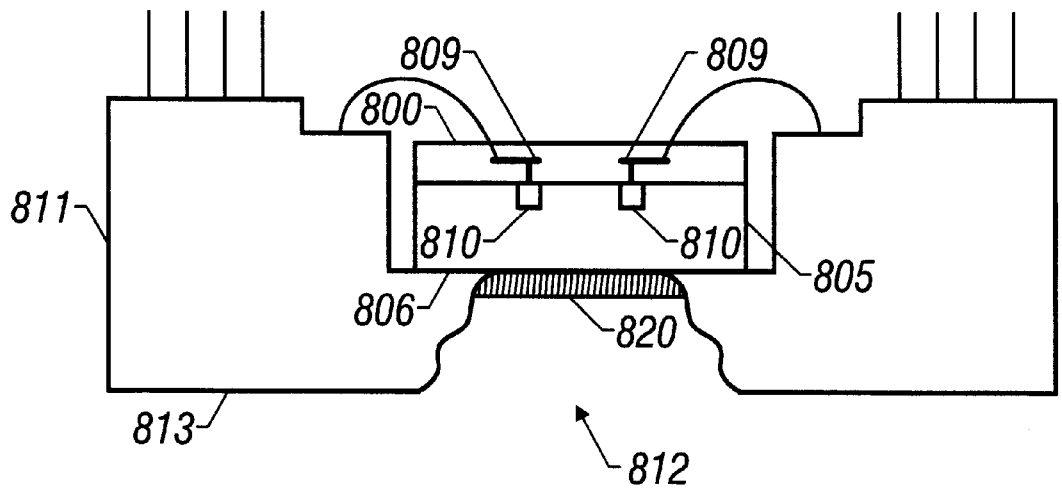
FIG. 8A illustrates a wire bonded semiconductor device in one embodiment of the present invention.

In the foregoing discussion, the use of an anti-reflective coating to enhance the optical-based testing and debugging of semiconductor devices has focused primarily on C4 packaged technology. It is appreciated, however, that the use of anti-reflective coatings to enhance optical-based testing may be used on any type of semiconductor device in which access to the back side of the semiconductor is obtainable. As shown in FIG. 8A, the back side surface 806 of a wire bonded semiconductor device 800 may be accessed by removing a portion of the device package 811. The back side surface 806 of the semiconductor substrate 805 may be exposed by cutting, etching or milling away the bottom surface 813 of package 811. Once the back side surface 806 of substrate 805 is exposed, an anti-reflective coating 820 is deposited onto the surface by any of a variety of deposition processes known in the art. It may be necessary to clean and/or polish back side surface 806 prior to depositing anti-reflective coating 820. A diffusion region 810, metal layer interconnect 809, or any other portion of the integrated circuit housed within device 800, may then be tested in accordance with any of a number of optical-based testing methodologies.

Figure 8B:
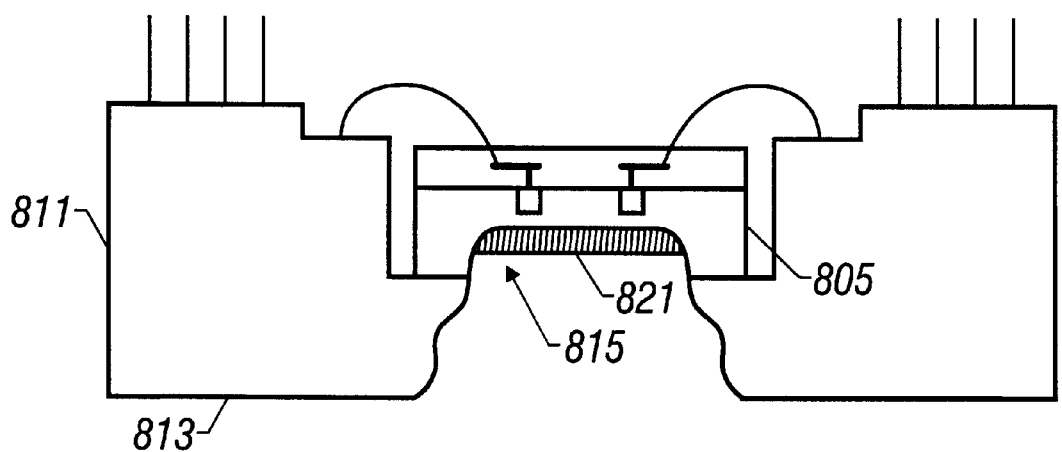
FIG. 8B illustrates the semiconductor device of FIG. 6A after the back side of the semiconductor has been thinned.

To further enhance the energy level of photons being emitted from the back side of semiconductor device 800, semiconductor substrate 805 may be globally or locally thinned prior to the application of anti-reflective coating 820, as shown in FIG. 8B. As previously discussed, since absorption losses through the semiconductor substrate are a function of the substrate thickness, absorption losses are reduced by thinning of the semiconductor substrate. In one embodiment, semiconductor substrate 805 is thinned and then polished to a smooth surface 806. In yet another embodiment, substrate 805 is thinned by first chemically etching and then polishing surface 806 to a smooth finish. Other processes known in the art, such as milling, may also be used to thin substrate 805.

Thus, what has been described is a method and an apparatus for reducing reflections off the surface of a semiconductor substrate. In the foregoing detailed description, the methods and apparatus of the present invention has been described with reference to specific exemplary embodiments thereof, and more particularly to integrated circuit devices that are housed within conventional integrated circuit packages. It is appreciated, however, that the present invention is not limited by the manner in which the integrated circuit is packaged. For instance, the methodology of the present invention may be used to test integrated circuit devices that are integrally formed within a printed circuit board. Moreover, it is evident that various modifications and changes may be made thereto without departing from the broader spirit and scope of the present invention. The present specification and figures are accordingly to be regarded as illustrative rather than restrictive.

What is claimed is:

1. A method of testing a portion of an integrated circuit formed on top of a semiconductor substrate, said method comprising:
   a) focusing a photon on said portion of said integrated circuit;
   b) passing said photon through an anti-reflective coating disposed on the back side of said semiconductor substrate such that the reflectivity of said photon is reduced; and,
   c) detecting said photon after said photon is reflected from said portion of said integrated circuit.

2. The method of claim 1 wherein said photon comprises a laser beam.

3. The method of claim 1 wherein said photon comprises thermal radiation.

4. The method of claim 1 wherein said photon comprises infrared light.

5. The method of claim 1 wherein said photon comprises a photon emission.

6. The method of claim 1 wherein said portion of said integrated circuit comprises a diffusion region of said integrated circuit.

7. The method of claim 1 wherein said portion of said integrated circuit comprises a segment of a metal interconnect line in a metal layer of said integrated circuit.

8. The method of claim 1 further comprising the step of thinning a portion of said semiconductor substrate located below said portion of said integrated circuit prior to focusing said photon onto said portion of said integrated circuit.

9. The method of claim 8 wherein said step of thinning said semiconductor substrate comprises the step of polishing said back side of said substrate.

10. The method of claim 8 wherein said step of thinning said semiconductor substrate comprises the step of etching said back side of said substrate.

11. The method of claim 8 wherein said step of thinning said semiconductor substrate comprises the step of milling said back side.

12. A method of testing a portion of an integrated circuit formed on top of a semiconductor substrate, said method comprising:
   a) depositing an anti-reflective coating onto the back side of the semiconductor substrate;
   b) focusing a photon on said portion of said integrated circuit through said anti-reflective coating;
   c) passing said photon through said anti-reflective coating such that the reflection of light off said semiconductor substrate is reduced; and,
   d) detecting said photon reflected from said portion of said integrated circuit.

13. The method of claim 12 wherein the step of depositing said anti-reflective coating includes evaporating an anti-reflective material onto said back side surface.

14. The method of claim 12 further comprising the step of thinning a portion of said semiconductor substrate located below said portion of said integrated circuit prior to depositing said anti-reflective coating.

15. The method of claim 14 wherein said step of thinning said semiconductor substrate comprises the step of polishing said back side of said substrate.

16. The method of claim 14 wherein said step of thinning said semiconductor substrate comprises the step of etching said back side of said substrate.

17. A method of testing a portion of an integrated circuit formed on top of a semiconductor substrate, said method comprising:
   a) depositing an anti-reflective coating onto the back side of the semiconductor substrate;
   b) passing said photon through said anti-reflective coating such that the reflectivity of said photon is reduced; and,
   c) detecting a photon emitted from said portion of said integrated circuit through said semiconductor substrate and said anti-reflective coating.

18. The method of claim 17 wherein the step of depositing said anti-reflective coating includes evaporating an anti-reflective material onto said back side surface.

19. The method of claim 17 wherein said photon comprises thermal radiation.

20. The method of claim 17 wherein said photon comprises infra-red light.

21. The method of claim 17 wherein said portion of said integrated circuit comprises a diffusion region of said integrated circuit.

22. The method of claim 17 wherein said portion of said integrated circuit comprises a segment of a metal interconnect line in a metal layer of said integrated circuit.

23. The method of claim 17 further comprising the step of thinning a portion of said semiconductor substrate located below said portion of said integrated circuit prior to depositing said anti-reflective coating.

* * * * *